United States Patent [19]

Schenck et al.

[11] Patent Number: 4,972,836
[45] Date of Patent: Nov. 27, 1990

[54] MOTION DETECTOR FOR HIGH-RESOLUTION MAGNETIC RESONANCE IMAGING

[75] Inventors: John F. Schenck, Schenectady, N.Y.; Steven P. Souza, Williamstown, Mass.; David R. Eisner, Schenectady, N.Y.

[73] Assignee: General Electric Company, Schenectady, N.Y.

[21] Appl. No.: 452,173

[22] Filed: Dec. 18, 1989

[51] Int. Cl.$^5$ .................. A61B 5/055; G01R 33/20
[52] U.S. Cl. ................... 128/653 A; 128/745; 128/780; 606/4; 351/209; 351/210
[58] Field of Search ............ 128/653 A, 665, 721, 128/745, 774, 782, 660.03; 606/4, 5, 6, 167, 169, 171, 172; 351/209, 210

[56] References Cited

U.S. PATENT DOCUMENTS

| | | | |
|---|---|---|---|
| 4,569,354 | 2/1986 | Shapiro et al. | 128/745 |
| 4,576,176 | 3/1986 | Myers | 128/661.06 |
| 4,585,011 | 4/1986 | Broughton et al. | 128/745 |
| 4,664,129 | 5/1987 | Helzel et al. | 128/721 |
| 4,719,912 | 1/1988 | Weinberg | 606/4 |
| 4,848,340 | 7/1989 | Bille et al. | 606/4 |

FOREIGN PATENT DOCUMENTS

| | | | |
|---|---|---|---|
| 0279589 | 8/1988 | European Pat. Off. | 128/745 |
| 3135070 | 3/1983 | Fed. Rep. of Germany | 128/653 R |
| 2604890 | 4/1988 | France | 128/653 SC |

*Primary Examiner*—Francis Jaworski
*Assistant Examiner*—Krista M. Pfaffle
*Attorney, Agent, or Firm*—Geoffrey H. Krauss; James C. Davis, Jr.; Marvin Snyder

[57] ABSTRACT

Apparatus for detecting movement of an anatomical sample undergoing NMR imaging uses at least one optical sensor, each having an output responsive to the intensity of received illumination and each directed to view a selected portion of sample; and apparatus for monitoring the output of each sensor to detect a change therein responsive to movement of the sample.

9 Claims, 4 Drawing Sheets

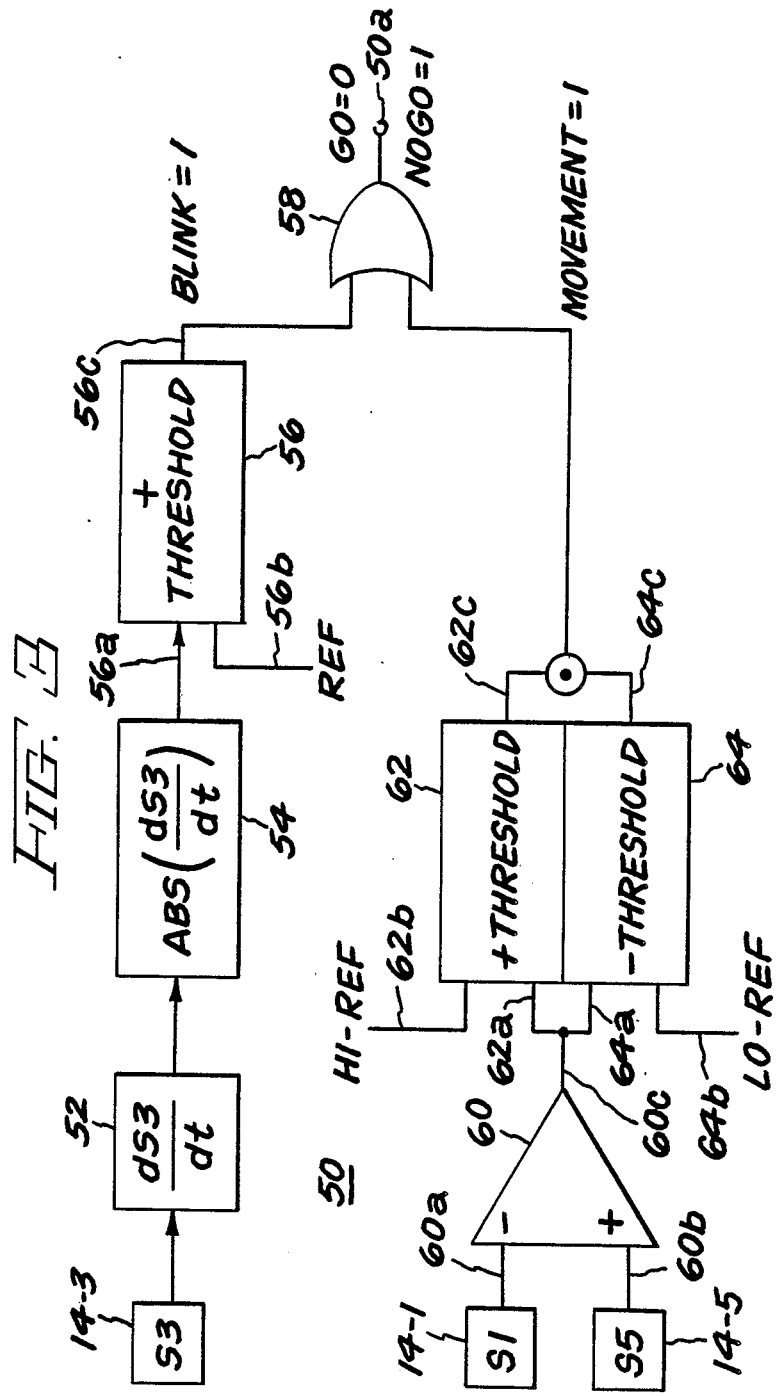

MOTION DETECTOR FOR HIGH-RESOLUTION MAGNETIC RESONANCE IMAGING

BACKGROUND OF THE INVENTION

The present invention relates to nuclear magnetic resonance (NMR) imaging and, more particularly, to a novel detector for determining when a portion-being-imaged is in motion, during a high-resolution NMR imaging procedure.

It is known that high-contrast magnetic resonance imaging of a portion of human anatomy, such as the eye, is possible. However, diagnosis of eye diseases by use of NMR imaging has been prevented due to certain technical limitations, so that radiologists frequently continue to use computed tomography examinations for eye studies in cases where magnetic resonance imaging (MRI) may potentially provide a higher contrast and more detailed image. In addition to the higher image quality potentially offered by MRI examinations, it is known that the x-ray dose attendant to computerized-tomography scanning is sufficiently large so that, in some cases, follow-up studies on any given patient are precluded. Conversely, MRI studies appear to be repeatable as often as necessary for a given patient. As described and claimed in our co-pending application Ser. No. 07/452,176, filed Dec. 18, 1989, assigned to the assignee of the present application and incorporated herein in its entirety by reference, we have developed specialized antennae to overcome some of the technical limitations for NMR imaging of the human eye and provide sensitivity and signal-to-noise ratio (SNR) characteristics which permit rapid high-resolution imaging of small structures (such as the lens, and the like) within the eye. While these receiver coils avoid the hitherto-encountered difficulties in awkwardness in placement of such reception coils in position and in maintenance in the placed position, even while being more easily tolerated by the patient during the MRI scanning process, some means must be provided to prevent data acquired when the anatomical portion has moved (such as when the patient's eye blinks or moves) from being included in the data set, as such inclusion will result in loss of resolution or other image imperfections, known as artifacts. Accordingly, a motion detector for determining when acquired data is not acceptable, is highly desirable.

BRIEF SUMMARY OF THE INVENTION

In accordance with the invention, apparatus for detecting movement of an anatomical sample undergoing NMR imaging, comprises: at least one optical sensor, each having an output responsive to the intensity of illumination thereon; means for directing each sensor to a selected portion of said sample; and means for monitoring the output of each sensor to detect a change therein responsive to movement of said sample.

In presently preferred embodiments, a plurality of optical sensors, each focused upon a different portion of the sample, are used. Differential measurement of the outputs of pairs of sensors provides more sensitive motion detection.

Accordingly, it is an object of the present invention to provide a novel motion detector for use in high-resolution NMR imaging.

This and other objects of the present invention will become apparent upon a reading of the following detailed description, when considered in conjunction with the associated drawings.

BRIEF DESCRIPTION OF THE DRAWINGS

FIG. 3 is a schematic block diagram of one possible electronics subassembly for processing the various photodetector output signals to determine when undesirable sample motion has occurred.

DETAILED DESCRIPTION OF THE INVENTION

Figure 1A:
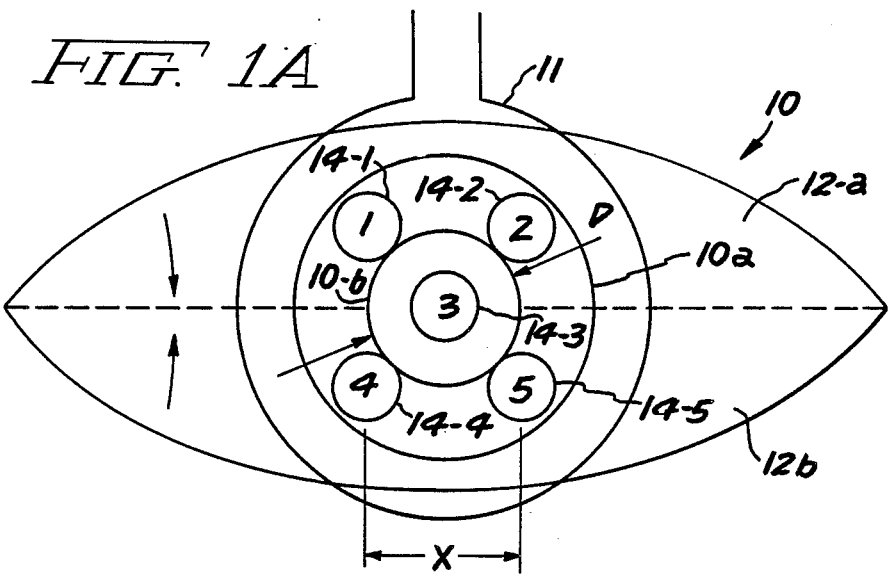
FIGS. 1A, 1B and 1C are front views of a portion of the eye of a patient undergoing NMR ocular imaging and illustrating both the movement/blink problem and several sensor-placement profiles for alleviation of the problem, with use of the apparatus of the present invention.

Referring initially to FIG. 1A, a sample 10, such as an eye, is to undergo NMR examination. In order for the resulting image to have a desired high resolution, a high-sensitivity response signal receptor 11, such as a surface coil and the like, must be properly positioned. Here, the coil 11 is shown as positioned to generally enclose the iris 10a of the patient's eye, for imaging of the anterior fine elements (cornea, lens, etc.) thereof. Because almost all NMR imaging procedures require a relative long time interval for completion, there is almost certainly going to be movement of the sample (eye) or of surrounding structures (such as blinking by closure of eyelids 12a/12b over the orb of the eye). Any movement/blinking causes a different structure to be present at any one location during one data-taking sequence, but not during other sequences; hence, erroneous data is present when the sample moves (e.g. eye movement or lid blink), and the data recovered during the presence of such movement can be discarded (a "no go" situation for data retention) and that portion of the sequence repeated until recovered data is retainable (e.g. a "go" situation, with little or no movement). Thus, it is desirable to provide the imaging system with a signal that tells whether the patient's eye is oriented properly and whether the patient has blinked. The NMR data acquisition consists of a repetitive sequence of signals received over a duration determined by the echo time, $T_E$ and repeated at periodic intervals determined by the interpulse or recovery time, $T_R$. The echo time used for eye imaging is usually in the range from 20 to 100 msec and the $T_R$ interval is determined by the details of the information desired from the image. It is usually in the range from 100 to 4000 msec. During each of the data acquisitions (there are usually either 128 or 256 of these) it is desirable that the eye and eyelid be in substantially the same position to avoid the presence of artifacts in the MR image.

In accordance with one aspect of the our invention, a plurality S of optical sensors 14a–14n are arranged about a sample portion so selected as to reflect incident light, to facilitate detection of movement by changes in reflection amplitude characteristics. Here S=5 sensors 14-1 through 14-5 are used, with a viewing field of a middle sensor 14-3 being directed at the center 10b (pupil) of the eye and the field of view of one of the other sensors 14-1, 14-2, 14-4 and 14-5 placed at corners of an imaginary square surrounding the central sensor, and with a separation distance X to have each sensor's field-of-view just touch the sample eye pupil 10b. Each corner sensor receives reflected light from the eye iris 10a, which is of a different reflectance from the pupil 10b, so that a change in output from one sensor will occur if the eye moves and a portion of the pupil moves into any part of a sensor's field-of-view previously occupied by the iris of that eye. Thus, the output of each corner sensor can be stored, as a reference level, when the eye is centered and located properly, and periodic comparisons of present sensor output to the reference level will indicate if movement occurs. Similarly, the central sensor 14-3 will provide a change in output if a blink occurs to the different reflection from the eyelids 12a/12b closed over the eye structure.

Figure 1B:
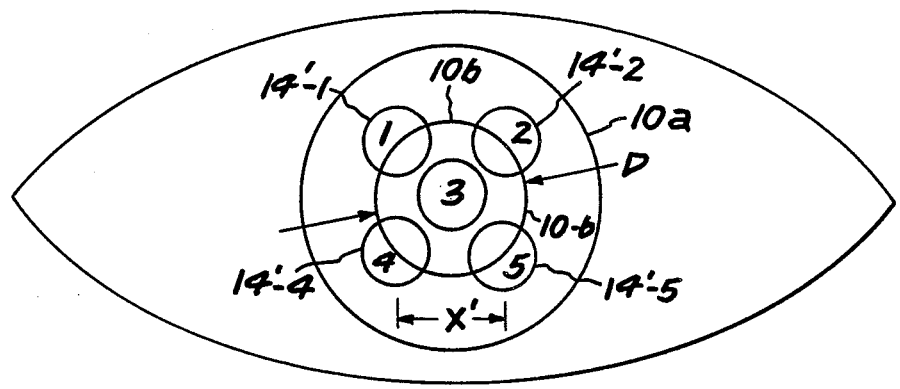
Figure 1C:
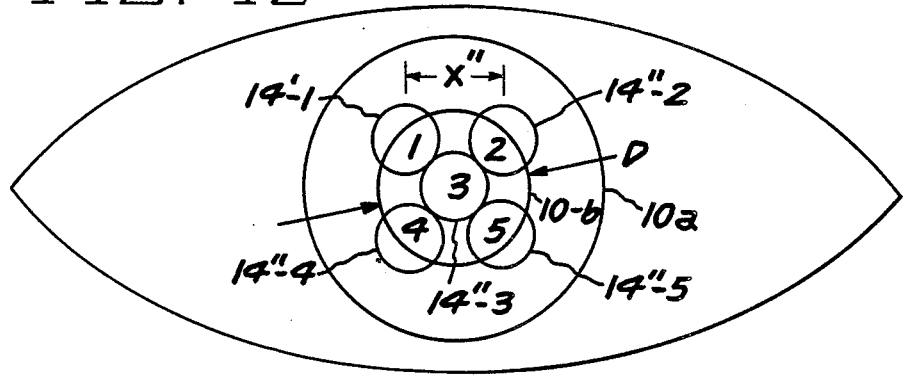

Referring now to FIG. 1B, the sensors 14'-1 through 14'-5 are, in this embodiment, closer together, so that the square side X' dimension is less than dimension X (in FIG. 1A) but larger than pupil diameter D. There is a portion of the field of view of each iris sensor 14'-1, 14'-2, 14'-4 and 14'-5 which is normally filled with pupil; thus, a greater sensitivity to movement may be possible. Similarly, a different pupil movement sensitivity is provided where each of the corner sensors 14"-1, 14"-2, 14"-4 and 14"-5 (FIG. 1C) has a field-of-view not only just touching the field-of-view of the center sensor 14"-3, but also having a minimum amount of view of iris 10a. Here, separation distance X" is less than X' and less than pupil diameter D. In some cases, center sensor 14"-3 may not be needed.

Figure 2A:
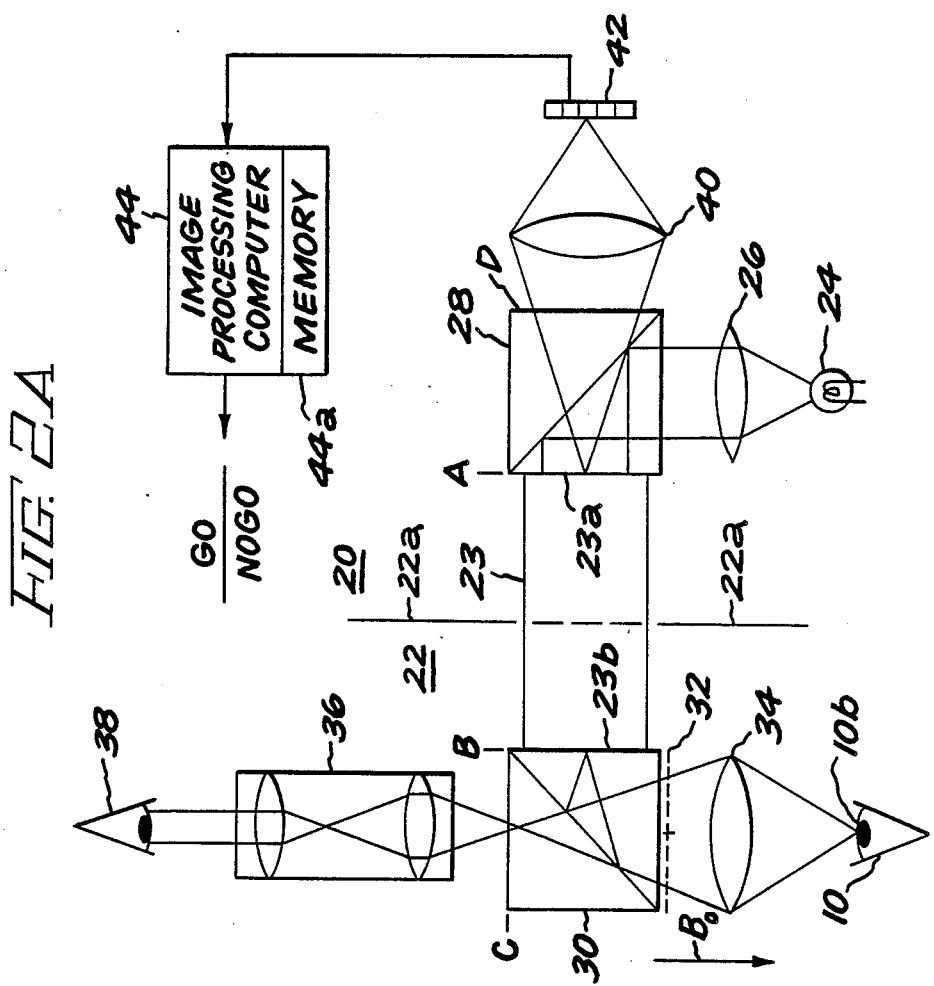
FIG. 2A is a schematic diagram of a first presently preferred embodiment of motion detection apparatus in accordance with the principle of the present invention.

Referring now to FIG. 2A, one embodiment of detection apparatus 20 is shown for detecting motion of a sample 10 undergoing NMR imaging. Sample 10 is inside the magnetic field $B_D$ of an NMR magnet 22, in which field conductive or magnetic material cannot be placed without great care; accordingly, non-magnetic and non-conductive optical components are used within magnet 22, with optical images brought out through wall 22a of the magnet via a fiber optic cable 23 and the like means. A light source 24 is collimated by lens means 26; a beam-splitting means 28 directs the collimated beam onto plane A. The illumination at plane A is passed from a first end 23a of transmission means 23 to the opposite end 23b thereof. At end 23b, the illumination impinges on plane B of another beam-splitting means 30. The beam is redirected through a reticle 32 and lens means 34 to illuminate sample (eye pupil) portion 10b. Part of the light reflected from sample 10 passes through plane C of the second beam splitter means 30, and thence through eyepiece 36, to allow observer 38 to move means 30/32/34 to focus the beam at the desired part (pupil 10b) of the sample 10. The rest of the reflected light passes through plane B, means 23 and plane A, through beam-splitting means 28, leaves plane D and is focused by lens means 40 on the optical sensors (e.g. photo diodes and associated current-to-voltage converters) of sensor array 42. It should be understood that means 23 is any means capable of transferring an optical real image between planes A and B; in an extreme case, means 23 may have essential zero length and plane A and plane B will be coincident. Means 23 can use lenses, mirrors and the like, instead of (or along with) fiberoptics means. Similarly, beamsplitting means 28 and 30 may be of any type and of any desired transmission/reflection ratio. The reticle 32 provides a spot at which the sample eye can stare; another reticle may be used, in plane C, to provide a reference pattern for aiding the operator 38 to align apparatus 20 with sample 10.

Figure 2B:
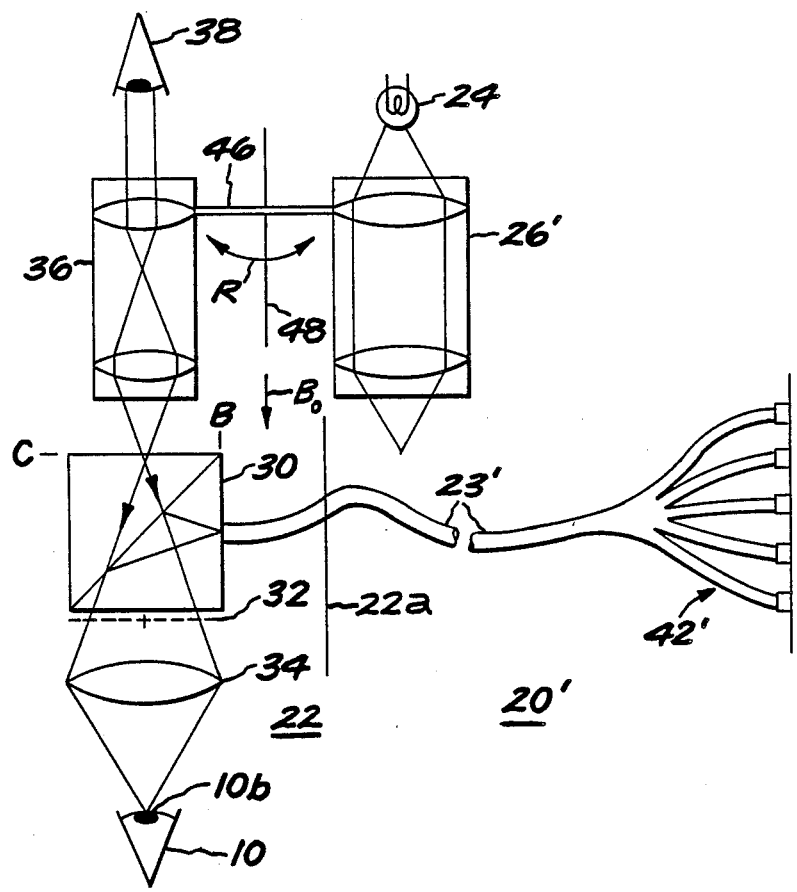
FIG. 2B is a schematic diagram of another presently preferred embodiment of our apparatus.

The presently preferred embodiment in FIG. 2B has apparatus 20' which is somewhat simpler than apparatus 20. Here, observer 38 uses eyepiece 36 to align the beamsplitter 30, reticle 32 and lens means 34 combination with sample 10, using available light. Thereafter, the eyepiece is exchanged for a light source 24—condenser 26' combination, e.g. by rotation of means 36/26' (attached to opposite ends of member 46) about pivot means 48, in the direction of arrows R. The light from source 24 passes through plane C of the beam-splitter splitter means 30 and illuminates sample 10. The reticle 32 aids the patient in maintaining eye alignment and minimizing movement. Light reflected from sample 10 is reflected by beamsplitter 30 to pass through plane B and into a bundle 23' of at least one (and typically 5) of fiberoptic cables, each of which leads to an associated one of an array 42' of photodiode-optical sensing means. After amplification and/or photocurrent-to-voltage conversion, if required, by well-known circuit means, other well-known means can be used to derive such signals as: the time derivative and time integral of each sensor output signal, the pair-wise, 3-way, etc. instantaneous sum and difference signals and their derivatives and integrals, and the absolute value of any of the signals.

FIG. 3 is the schematic block diagram of one electronics subassembly 50 which can operate on the output of several sensors (here, center S3 sensor 14-3 and opposed-corner S1 and S5 sensors 14-1 and 14-5) for respectively detecting blink (lid movement) and eye movement. We detect an eye-blink by first differentiating, with respect to time, the output of the center S3 sensor 14-3, in differentiator means 52. The absolute valve of the differentiated signal is taken in absolute-value ABS means 54. The ABS signal is always a positive-polarity signal, at an input 56a of a positive threshold means 56, which provides a logic "1" signal at an output 56c if the input 56a signal amplitude exceeds a reference REF value at another input 56b. This "BLINK" no-go logic one signal can be applied to one input of a logic-OR gate 58. Eye movement may be detected by taking the difference between the signals from the corner sensors (here, S1 sensor 14-1 and S5 sensor 14-5) connected respectively to an inverting input 60a and a non-inverting input 60b of a differential amplifier 60. The differential signal at output 60c is applied to inputs 62a and 64a of a pair of threshold means 62/64, where the signal amplitude is compared to a high-level reference at input 62b and a low-level reference at input 64b. If the differential sensor signal becomes either greater than the HI-REF level (actuating output 62c) or less than the LO-REF level (actuating output 64c), then a logic-one signal, signifying eye movement, is sent to gate 58. Thus, the gate output (at subassembly output 50a), will normally be at a logic zero level, unless a blink or eye movement is detected, to change the output 50a level to a logic-one signal. This signal can be used to ignore the data then being taken, and to start a new data acquisition attempt with the previous parameters. It will be understood that the opposite diagonal (sensors S2 and S4) can be processed and used in similar manner.

While several presently preferred embodiments of our novel invention have been described in detail herein, many modifications and variations will now become apparent to those skilled in the art. It is our intent, therefore, to be limited only by the scope of the appending claims and not by the specific details and instrumentalities presented by way of explanation herein.

We claim:

1. In a Magnetic Resonance Imaging system having a magnet which produces a magnetic field, an apparatus for detecting movement of an anatomical sample and undergoing NMR analysis, said apparatus comprising:
   means for illuminating said sample;
   a plurality of sensors, each located outside of an imaging volume of said magnet, for receiving reflected illumination from the sample, and each of said sensors having an output responsive to said reflected illumination;
   means for directing a field-of-view of each of said sensors to a selected portion of said sample within said imaging volume and
   means for monitoring the output of each of said sensors to detect a change in the amount of said reflected illumination received responsive to the movement of said sample.

2. The apparatus of claim 1, wherein said monitoring means compares a present output of at least one of said sensors against a stored reference level therefore, and indicates that movement has occurred if the present output has deviated from the stored reference level by a preselected amount.

3. The apparatus of claim 1, wherein said monitoring means includes: means for obtaining a difference between signals from a pair of said sensors; and means for comparing the difference to a pair of high and low reference levels, to determine if movement has occurred.

4. The apparatus of claim 1, wherein said monitoring means includes: means for time differentiating the output of a selected one of the plurality of said sensors, to provide a differentiated signal; means for obtaining an absolute value of the differentiated signal, to provide an absolute-valued signal; and means for thresholding the absolute-valued signal against a reference level to determine if movement has occurred.

5. In a Magnetic Resonance Imaging system having a magnet which produces a magnetic field, an apparatus for determining movement of an eye undergoing NMR analysis, said apparatus comprising:
   means for illuminating selected area of said eye;
   means located outside of an imaging volume of said magnet for sensing the illumination from the selected area and providing at least one selected signal responsive to the amplitude thereof;
   means for focusing the sensed illumination from each of said selected areas of said eye upon a different one of said sensing means; and
   means operating upon the amplitude of at least one of said selected sensor signals for detecting eye movement by a change in said amplitude.

6. The apparatus of claim 5, wherein at least one sensing means is focused upon a pupil of said eye.

7. The apparatus of claim 6, wherein said operating means includes: means for providing a first signal proportional to a time-derivative of said at least one sensing means; means for providing another signal proportional to an absolute value of said first signal; and means for comparing said another signal to a reference signal to determine if said eye has blinked.

8. The apparatus of claim 5, wherein said sensing means includes at least a pair of sensors, each of said sensors being focused upon a different one of diagonally-opposed portions of said eye.

9. The apparatus of claim 8, wherein said operating means includes: means for obtaining a difference between signals from said pair of sensors; and means for comparing the difference to a pair of high and low reference levels, to determine if eye movement has occurred.

* * * * *